US008267891B2

(12) United States Patent
Dimalanta et al.

(10) Patent No.: US 8,267,891 B2
(45) Date of Patent: Sep. 18, 2012

(54) GILLED PHACOEMULSIFICATION IRRIGATION SLEEVE

(75) Inventors: Ramon Dimalanta, Trabuco Canyon, CA (US); Grace Liao, Irvine, CA (US)

(73) Assignee: Alcon Research, Ltd., Fort Worth, TX (US)

(*) Notice: Subject to any disclaimer, the term of this patent is extended or adjusted under 35 U.S.C. 154(b) by 109 days.

(21) Appl. No.: 12/338,305

(22) Filed: Dec. 18, 2008

(65) Prior Publication Data

US 2010/0160851 A1 Jun. 24, 2010

(51) Int. Cl.
*A61M 1/00* (2006.01)

(52) U.S. Cl. .............. 604/118; 604/30; 604/167.04; 604/246; 604/247; 604/256; 604/264

(58) Field of Classification Search .......... 604/27, 604/30, 31, 35, 118, 119, 129, 167.01, 167.02, 604/167.03, 167.04, 246, 247, 256, 264
See application file for complete search history.

(56) References Cited

U.S. PATENT DOCUMENTS

| 645,530 | A | 3/1900 | Marston |
|---|---|---|---|
| 3,805,787 | A | 4/1974 | Banko |
| 4,643,717 | A | 2/1987 | Cook et al. |
| 4,681,561 | A | 7/1987 | Hood et al. |
| 4,787,889 | A | 11/1988 | Steppe et al. |
| 4,808,154 | A | 2/1989 | Freeman |
| 4,816,017 | A | 3/1989 | Hood et al. |
| 4,867,141 | A | 9/1989 | Nakada et al. |
| 4,867,747 | A | 9/1989 | Yarger |
| 4,897,079 | A | 1/1990 | Zaleski et al. |
| 4,973,319 | A * | 11/1990 | Melsky ................ 604/247 |
| 4,973,321 | A | 11/1990 | Michelson |
| 4,983,160 | A | 1/1991 | Steppe et al. |
| 5,030,210 | A * | 7/1991 | Alchas ................ 604/247 |
| 5,038,756 | A | 8/1991 | Kepley |
| 5,084,009 | A | 1/1992 | Mackool |
| 5,123,903 | A | 6/1992 | Quaid et al. |
| 5,188,589 | A | 2/1993 | Wypych et al. |
| 5,199,943 | A | 4/1993 | Wypych |
| 5,255,669 | A | 10/1993 | Kubota et al. |
| 5,282,786 | A | 2/1994 | Ureche |
| 5,286,256 | A | 2/1994 | Mackool |
| 5,346,502 | A | 9/1994 | Estabrook et al. |

(Continued)

FOREIGN PATENT DOCUMENTS

EP 0352984 4/1994

(Continued)

OTHER PUBLICATIONS

International Search Report for PCT/US2009/067860, Publication No. WO2010/080356, 4 pages, Mar. 19, 2010.

(Continued)

*Primary Examiner* — Bhisma Mehta
(74) *Attorney, Agent, or Firm* — Darien Reddick (57) ABSTRACT

A phacoemulsification irrigation sleeve includes an elongated, resilient, tubular body section configured to surround a portion of a shaft of a phacoemulsification needle, the tubular body section having a distal end and a proximal end, and an inner surface and an outer surface. An enlarged section formed on the proximal end of the tubular body portion surrounds a hub of the phacoemulsification needle and connects the irrigation sleeve to a phacoemulsification handpiece. The irrigation sleeve further comprises at least one slitted irrigation port formed adjacent to the distal end of the body section and configured to splay in response to a drop in pressure between the inner surface and the outer surface.

10 Claims, 5 Drawing Sheets

U.S. PATENT DOCUMENTS

| | | | |
|---|---|---|---|
| 5,354,265 A | 10/1994 | Mackool | |
| 5,397,293 A | 3/1995 | Alliger et al. | |
| 5,413,556 A | 5/1995 | Whittingham | |
| 5,486,162 A | 1/1996 | Brumbach | |
| 5,505,693 A | 4/1996 | Mackool | |
| 5,562,609 A | 10/1996 | Brumbach | |
| 5,634,912 A | 6/1997 | Injev | |
| 5,645,530 A | 7/1997 | Boukhny et al. | |
| 5,725,495 A | 3/1998 | Strukel et al. | |
| 5,741,226 A | 4/1998 | Strukel et al. | |
| 5,743,871 A | 4/1998 | Strukel et al. | |
| 5,807,310 A | 9/1998 | Hood | |
| 5,830,192 A | 11/1998 | Van Voorhis | |
| 5,873,851 A | 2/1999 | Nilsson | |
| 5,919,157 A | 7/1999 | Strukel | |
| 5,941,887 A | 8/1999 | Steen et al. | |
| 5,984,904 A | 11/1999 | Steen et al. | |
| 6,013,046 A | 1/2000 | Maaskamp et al. | |
| 6,033,376 A | 3/2000 | Rockley | |
| 6,056,735 A | 5/2000 | Okada et al. | |
| 6,117,151 A | 9/2000 | Urich et al. | |
| 6,132,436 A | 10/2000 | Portney | |
| 6,132,448 A | 10/2000 | Perez et al. | |
| 6,159,175 A | 12/2000 | Strukel et al. | |
| 6,224,565 B1 | 5/2001 | Cimino | |
| 6,299,591 B1 | 10/2001 | Banko | |
| 6,361,520 B1 | 3/2002 | Rockley | |
| 6,398,754 B1 | 6/2002 | Sutton et al. | |
| 6,428,501 B1 | 8/2002 | Reynard | |
| 6,520,929 B2 | 2/2003 | Zaleski | |
| 6,605,054 B2 | 8/2003 | Rockley | |
| 6,613,056 B1 | 9/2003 | Brumbach et al. | |
| 7,014,629 B2 | 3/2006 | Mackool | |
| 7,063,680 B2 | 6/2006 | Lee et al. | |
| 7,066,923 B2 | 6/2006 | Tjia | |
| 7,094,229 B2 | 8/2006 | Boukhny et al. | |
| 7,445,596 B2 | 11/2008 | Kucklick et al. | |
| 7,500,947 B2 | 3/2009 | Kucklick et al. | |
| 7,601,136 B2 | 10/2009 | Akahoshi | |
| 7,704,244 B2 | 4/2010 | Boukhny et al. | |
| 2001/0034504 A1 | 10/2001 | Zaleski | |
| 2002/0091351 A1 | 7/2002 | Rockley | |
| 2002/0165492 A1* | 11/2002 | Davey et al. | 604/167.04 |
| 2005/0245886 A1 | 11/2005 | Devine et al. | |
| 2005/0283122 A1* | 12/2005 | Nordgren | 604/247 |
| 2008/0300531 A1 | 12/2008 | Gills, Jr. | |
| 2008/0319378 A1 | 12/2008 | Ponsi | |
| 2009/0043165 A1 | 2/2009 | Kucklick et al. | |
| 2009/0093750 A1* | 4/2009 | Herman | 604/22 |
| 2011/0092888 A1 | 4/2011 | Gerg | |
| 2011/0319810 A1 | 12/2011 | Ghannoum | |

FOREIGN PATENT DOCUMENTS

| | | |
|---|---|---|
| EP | 0778750 | 10/2003 |
| EP | 1568339 | 8/2005 |
| JP | 10-71166 | 3/1998 |
| JP | 2000-33097 | 2/2000 |
| WO | WO 96/27334 | 9/1996 |
| WO | WO 98/16155 | 4/1998 |
| WO | WO 99/62411 | 12/1999 |
| WO | WO 2005/110509 | 11/2005 |
| WO | WO 2006/105283 | 10/2006 |
| WO | WO 2009/046413 | 4/2009 |

OTHER PUBLICATIONS

International Preliminary Report on Patentability and the Written Opinion of the International Searching Authority, Issued Jun. 21, 2011 for Application No. PCT/US2009/067860, Filed Dec. 14, 2009; Publication No. WO2010/080356, Published Jul. 15, 2010, 6 pages.

* cited by examiner

GILLED PHACOEMULSIFICATION IRRIGATION SLEEVE

TECHNICAL FIELD

The present invention relates generally to phacoemulsification devices used in ophthalmic surgery, and more specifically relates to phacoemulsification irrigation sleeves.

BACKGROUND

The human eye functions to provide vision by transmitting light through a clear outer portion called the cornea, and focusing the image by way of a crystalline lens onto a retina. The quality of the focused image depends on many factors including the size and shape of the eye, and the transparency of the cornea and the lens. When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. A typical surgical handpiece suitable for phacoemulsification procedures consists of an ultrasonically driven phacoemulsification handpiece, an attached hollow cutting needle surrounded by an irrigating sleeve, and an electronic control console. The handpiece assembly is attached to the control console by an electric cable and flexible tubing. Through the electric cable, the console varies the power level transmitted by the handpiece to the attached cutting needle. The flexible tubing supplies irrigation fluid to the surgical site and draws aspiration fluid from the eye through the handpiece assembly.

The operative part in a typical handpiece is a centrally located, hollow resonating bar or horn directly attached to a set of piezoelectric crystals. The crystals supply the required ultrasonic vibration needed to drive both the horn and the attached cutting needle during phacoemulsification, and are controlled by the console. The crystal/horn assembly is suspended within the hollow body or shell of the handpiece by flexible mountings. The handpiece body terminates in a reduced diameter portion or nosecone at the body's distal end. Typically, the nosecone is externally threaded to accept the hollow irrigation sleeve, which surrounds most of the length of the cutting needle. Likewise, the horn bore is internally threaded at its distal end to receive the external threads of the cutting tip. The irrigation sleeve also has an internally threaded bore that is screwed onto the external threads of the nosecone. The cutting needle is adjusted so that its tip projects only a predetermined amount past the open end of the irrigating sleeve.

During the phacoemulsification procedure, the tip of the cutting needle and the end of the irrigation sleeve are inserted into the anterior capsule of the eye through a small incision in the outer tissue of the eye. The surgeon brings the tip of the cutting needle into contact with the lens of the eye, so that the vibrating tip fragments the lens. The resulting fragments are aspirated out of the eye through the interior bore of the cutting needle, along with irrigation solution provided to the eye during the procedure, and into a waste reservoir.

Throughout the procedure, irrigating fluid is pumped into the eye, passing between the irrigation sleeve and the cutting needle and exiting into the eye at the tip of the irrigation sleeve and/or from one or more ports, or openings, cut into the irrigation sleeve near its end. This irrigating fluid is critical, as it prevents the collapse of the eye during the removal of the emulsified lens. The irrigating fluid also protects the eye tissues from the heat generated by the vibrating of the ultrasonic cutting needle. Furthermore, the irrigating fluid suspends the fragments of the emulsified lens for aspiration from the eye.

A common complication during the phacoemulsification process arises from a blockage, or occlusion, of the aspirating needle. As the irrigation fluid and emulsified tissue is aspirated away from the interior of the eye through the hollow cutting needle, pieces of tissue that are larger than the diameter of the needle's bore may become clogged in the needle's tip. While the tip is clogged, vacuum pressure builds up within the tip. The resulting drop in pressure in the anterior chamber in the eye when the clog is removed is known as post-occlusion surge. This post-occlusion surge can, in some cases, cause a relatively large quantity of fluid and tissue to be aspirated out of the eye too quickly, potentially causing the eye to collapse and/or causing the lens capsule to be torn.

Various techniques have been attempted to reduce this surge, such as by venting the aspiration line or otherwise limiting the buildup of negative pressure in the aspiration system. However, there remains a need for improved phacoemulsification devices, including irrigation sleeves that reduce post-occlusion surge.

SUMMARY

Embodiments of the current invention include a phacoemulsification irrigation sleeve that has added slits, or "gills", aside from the holes or other outlets generally used to allow irrigation to flow into the anterior chamber of the eye. One effect of these slitted irrigation ports is to momentarily increase the maximum irrigation flow in response to the loss of pressure in the anterior chamber of the eye caused by post-occlusion surge. The temporarily increased irrigation flow afforded by the slitted irrigation ports offsets the loss of pressure, and minimizes the loss of fluid volume in the anterior chamber. When a sudden pressure drop in the anterior chamber of the eye draws the maximum amount of fluid from the ordinary irrigation ports in an irrigation sleeve, the gills will splay, spreading open to allow even more flow. This additional flow is supplied rapidly, in response to the temporarily increased demand, and is only supplied for the time that it is needed, thus preventing excessive volume and pressure within the anterior chamber.

An exemplary phacoemulsification irrigation sleeve according to some embodiments of the invention thus includes an elongated, resilient, tubular body section configured to surround a portion of a shaft of a phacoemulsification needle, the tubular body section having a distal end and a proximal end, and an inner surface and an outer surface. An enlarged section formed on the proximal end of the tubular body portion is configured to surround a hub of said phacoemulsification needle and for connection to a phacoemulsification handpiece. The irrigation sleeve further comprises at least one slitted irrigation port formed adjacent to the distal end of the body section and configured to splay in response to a drop in pressure between the inner surface and the outer surface.

In various embodiments, a slitted irrigation port may be a linear slit oriented longitudinally on the tubular body section, a linear slit oriented at approximately forty-five degrees relative to the longitudinal axis of the tubular body section, an arc-shaped slit, or a chevron-shaped slit. Other shapes and arrangements are also possible. In some embodiments, the at least one slitted irrigation port comprises an open portion configured to allow a first flow of irrigation fluid during a phacoemulsification procedure and a slitted portion configured to allow an increased flow of irrigation fluid, relative to the first flow, in response to a drop in pressure between the inner surface and the outer surface of the tubular body section. In still other embodiments, the at least one slitted irrigation port comprises a flap overlapping a portion of the outside surface of the tubular body section, such that the flap is configured to open in response to a drop in pressure between the inner surface and the outer surface. Any of the previously described embodiments might also comprise at least one thinned region adjacent to the at least one slitted irrigation portion.

Of course, those skilled in the art will appreciate that the present invention is not limited to the above features, advantages, contexts or examples, and will recognize additional features and advantages upon reading the following detailed description and upon viewing the accompanying drawings.

DETAILED DESCRIPTION

As summarized above, embodiments of the current invention include a phacoemulsification irrigation sleeve that has added slits, or "gills", aside from the holes or other outlets generally used to allow irrigation to flow into the anterior chamber of the eye. One effect of these slitted irrigation ports is to momentarily increase the maximum irrigation flow in response to the loss of pressure in the anterior chamber of the eye caused by post-occlusion surge. The temporarily increased irrigation flow afforded by the slitted irrigation ports offsets the loss of pressure, and minimizes the loss of fluid volume in the anterior chamber.

With appropriately designed slits or gills, when a sudden pressure drop in the anterior chamber of the eye draws the maximum amount of fluid from the ordinary irrigation ports in an irrigation sleeve, the gills will splay, spreading open to allow even more flow. This additional flow is supplied rapidly, in response to the temporarily increased demand, and is only supplied for the short time that it is needed, thus preventing excessive volume and pressure within the anterior chamber.

The slitted irrigation ports may vary in number and shape. For instance, the slits may comprise straight lines oriented along the longitudinal axis of the irrigation sleeve, or may be angled. In other embodiments, the slits may be shaped as arcs, angles, chevrons, etc. Some embodiments may include mixtures of any of these types, allowing a designer to finely tune responsiveness of the slitted irrigation ports to variations in pressure, while maintaining necessary structural integrity of the irrigation sleeve. In some embodiments, the slitted irrigation ports may be designed to allow additional flow through the thinning of the irrigation sleeve at the location of the slits, and/or through the provision of an overlapping flap, or "curtain," of material at the slitted irrigation port.

Those skilled in the art will appreciate that the benefits conferred by the inventive techniques and structures disclosed herein can be more significant for smaller sleeve designs (e.g., Alcon Laboratories' Ultrasleeve and Nanosleeve products) that are intended for use in smaller incisions (e.g., <2.4 mm). Because of their small size, these sleeves already have a compromised irrigation allowance, as compared to their predecessors. Accordingly, accommodating post-occlusion surge is more difficult for these smaller devices.

Larger irrigation sleeve diameter, larger holes, or multihole designs are generally the accepted solutions for increasing irrigation flow. Of course, with the current trends towards even smaller incision sizes, larger irrigation sleeves are not an option. Accordingly, in order to accommodate the maximum irrigation flows needed during post-occlusion surge, small sleeve designs require additional irrigation pathways to allow higher irrigation flows. However, the dimensions of holes for conventional irrigation ports in an irrigation sleeve are limited by the overall size of the sleeve itself. Furthermore, large holes may cause structural problems, so that the sleeve may lose its form during insertion or operation if the holes are excessively large. Additional holes to accommodate the maximum flow of irrigation fluid at all times may also increase turbulence and cause more chaotic flow patterns within the anterior chamber of the eye.

Another possible approach to the increased demand for irrigation fluid during post-occlusion surge is to increase the pressure of the irrigation supply, to allow more flow as needed. However, this approach comes with the risk of increasing the maximum pressure to the eye, when the demand for increased flow stops.

Accordingly, those skilled in the art will appreciate that one advantage of the phacoemulsification irrigation sleeves described herein is that, unlike the case with simple multihole configurations, the slitted irrigation ports only allow additional irrigation flow when higher flow rates are demanded—generally only when occlusion break and the resulting post-occlusion surge occur. By matching the number and size of conventional irrigation ports to the irrigation flow required during normal circumstances, rather than sizing these conventional ports for the maximum flows required during post-occlusion surge, the baseline irrigation flow can be designed to be more predictable, and to generate less turbulence in the eye. Because the slitted irrigation ports require the removal of less sleeve material than a conventional irrigation port, maintaining the structural integrity of the irrigation sleeve is also simplified.

With the preceding discussion in mind, those skilled in the art will appreciate that FIGS. 1-9 illustrate non-limiting examples of the present invention. As such, these illustrations depict only a few variations of the inventive phacoemulsification irrigation sleeves contemplated herein, and are presented only to aid in understanding the present invention.

Figure 1:
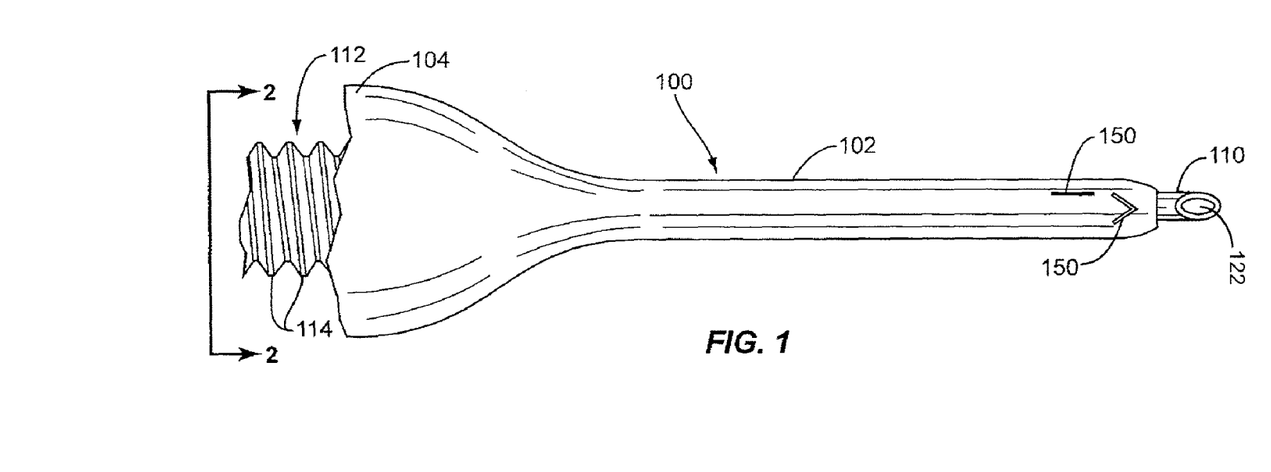
FIG. 1 is a side elevation view of a phacoemulsification needle inserted into a phacoemulsification irrigation sleeve, in accordance with some embodiments of the present invention.
Figure 2:
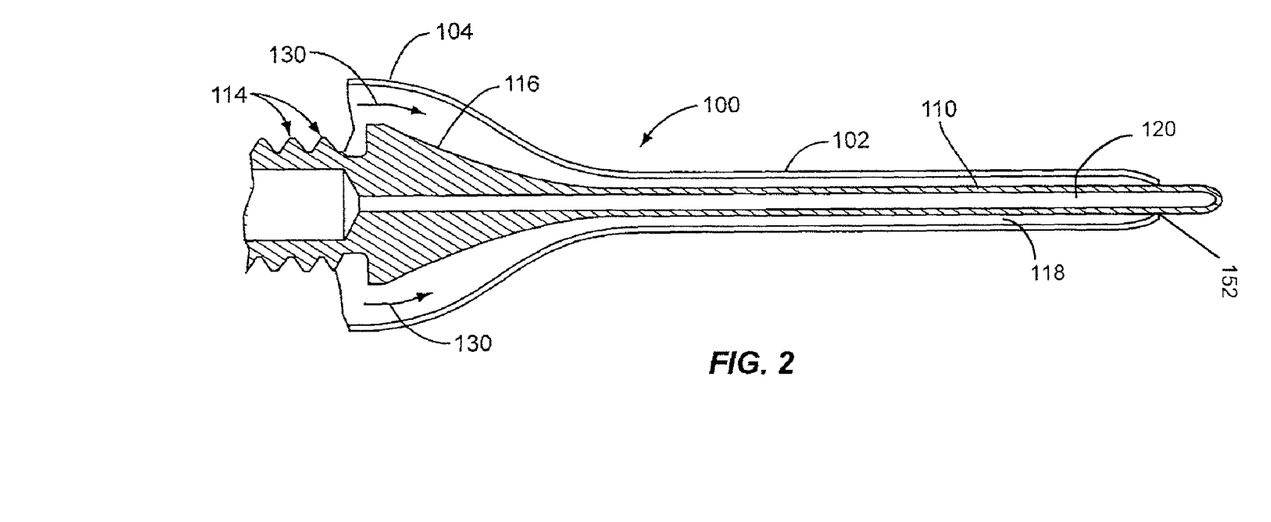
FIG. 2 is a cut-away side elevation of FIG. 1, taken along line 2-2.

FIGS. 1 and 2 provide a side elevation view and a cut-away view, respectively, of a phacoemulsification needle 110 installed within an exemplary phacoemulsification irrigation sleeve 100. Irrigation sleeve 100 includes an elongated, resilient tubular body portion 102, which is configured to surround all but a small portion of the hollow shaft of the needle 110. Accordingly, the tip of the needle 110 extends beyond the distal end of the irrigation sleeve 100. Additionally, the needle 110 includes a lumen 120 that defines an opening 122 formed at a distal end of the needle 110. The irrigation sleeve further comprises an enlarged section 104, which extends from the proximal end of the tubular body portion 102 and is configured to surround the hub 112 and flared portion 116 of the phacoemulsification needle 110. As with conventional irrigation sleeves, irrigation sleeve 100 may be formed of silicone, or other pliable, resilient material suitable for use in ophthalmic surgery. Furthermore, the general dimensions of irrigation sleeve 100 may correspond generally to conventional irrigation sleeves, for compatibility with existing phacoemulsification needles. As with conventional irrigation sleeves, irrigation sleeve 100 is thus generally suitable for insertion through a small incision in a patient's eye (e.g., an incision less than 2 mm in length), and serves to insulate the vibrating phacoemulsification needle 110 from eye tissue and to effectively seal the incision during the phacoemulsification procedure. The irrigation sleeve 100 may also include an opening 152 formed at the distal end of the tubular body section 102. The opening 152 may be adapted to accommodate a portion of the shaft of the phacoemulsification needle 110 extending through the opening 152.

In use, the hub 112 of the phacoemulsification needle 110 is screwed into a phacoemulsification handpiece (not shown), using threads 114. The enlarged section 104 of the irrigation sleeve also attaches to the phacoemulsification handpiece according to conventional techniques, in some cases using internal threads (not shown) formed inside the enlarged section 104 of the irrigation sleeve 100. The space between the irrigation sleeve 100 and the needle 110 thus forms a channel 118 through which irrigation fluid flows in the direction indicated by arrows 130. Irrigation fluid flows through the channel 118, towards the distal end of the irrigation sleeve 100, and in various embodiments exits the apparatus, into the eye, through a space between the distal end of the irrigation sleeve 100 and the phacoemulsification needle 110, or through one or more conventional irrigation ports (not shown), or both. Irrigation fluid and emulsified lens tissue is aspirated away from the eye, through the hollow needle 110, using a suction force applied through the phacoemulsification handpiece.

Phacoemulsification irrigation sleeve 100 includes several slitted irrigation ports 150. Two such slitted irrigation ports 150 are visible in the embodiment illustrated in FIG. 1, and in the corresponding detailed view of FIG. 3; those skilled in the art will appreciate that the number, positions, and detailed design of the slitted irrigation ports 150 may vary from one embodiment to another. Those skilled in the art will further appreciate that various embodiments of the irrigation sleeves described herein may further comprise one or more conventional irrigation ports (i.e., holes) in addition to one or more slitted irrigation ports 150. In these embodiments, the conventional irrigation ports are dimensioned and positioned to provide a "baseline" flow of irrigation fluid adequate to meet the normal demands of the procedure, while the slitted irrigation ports provide extra flow as needed, such as in response to a post-occlusion surge.

Figure 3:
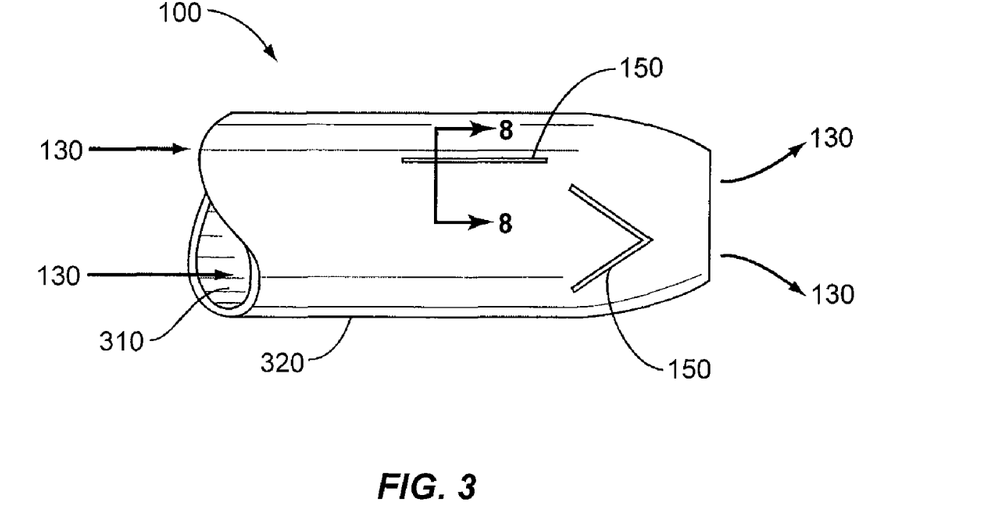
FIG. 3 is a detailed view of the tip of one embodiment of a phacoemulsification irrigation sleeve according to the present invention.

In the detailed view of FIG. 3, irrigation fluid flows inside the irrigation sleeve 100 in the direction indicated by the arrows 130, emerging at the distal end of the irrigation sleeve 100 from a space between the irrigation sleeve 100 and the needle 110. (The needle 110 is omitted from FIGS. 3-7 for clarity.) In other embodiments, irrigation fluid might exit into the eye from one or more conventional irrigation ports disposed along the tubular section of the irrigation sleeve 100, instead of or in addition to exiting from the end of the sleeve.

Figure 4:
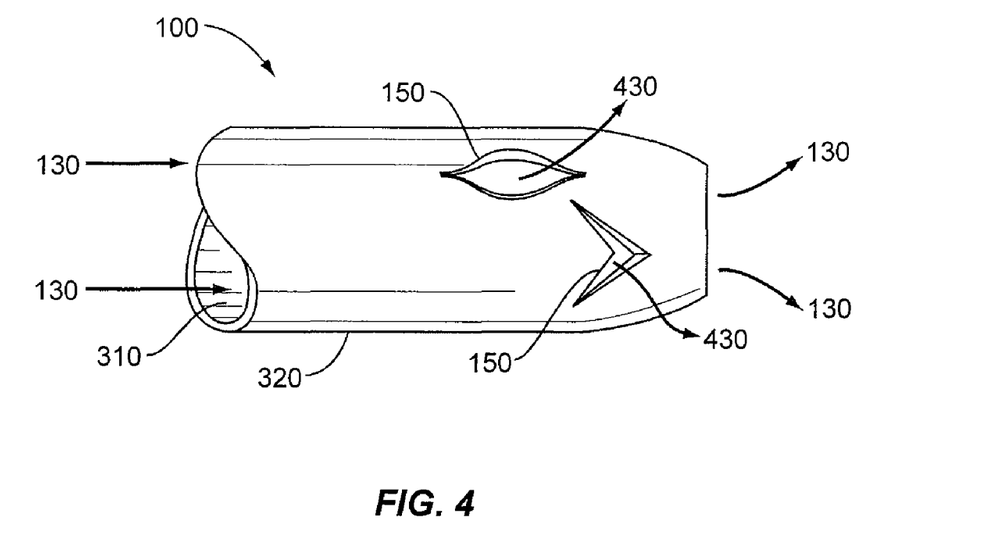
FIG. 4 illustrates the phacoemulsification irrigation sleeve of FIG. 3 with the slitted irrigation ports in a splayed configuration.

In FIG. 3, no significant quantity of irrigation fluid is exiting from slitted irrigation ports 150. This represents the "normal" state for the apparatus, in which an adequate flow of irrigation fluid is supplied to the surgical site, so that the pressure differential between the sleeve's inside surface 310 and outside surface 320 is low. FIG. 4, on the other hand, illustrates the response of the slitted irrigation ports 150 to a drop in pressure in the anterior chamber of the eye, such as the sudden drop in pressure that occurs when an occlusion breaks free or is removed from the aspirating tip of needle 110. When this occurs, the slitted irrigation ports splay, i.e., open up, in response to the drop in pressure, permitting an additional flow of irrigation fluid as indicated by arrows 430. Those skilled in the art will agree that the extent of splaying of the slitted irrigation ports 150 will generally vary with the demand for irrigation fluid, so that the slitted irrigation ports 150 serve to regulate the pressure in the anterior chamber of the eye.

Figure 5:
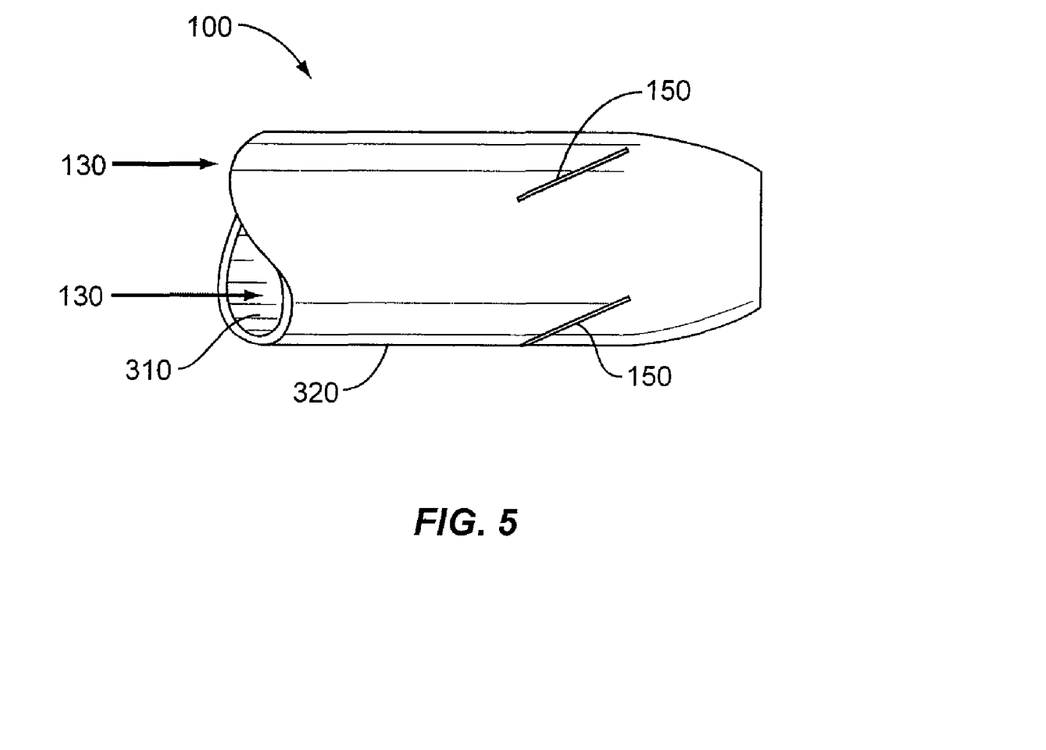
FIG. 5 is a detailed view of the tip of another embodiment of a phacoemulsification irrigation sleeve according to the present invention.
Figure 6:
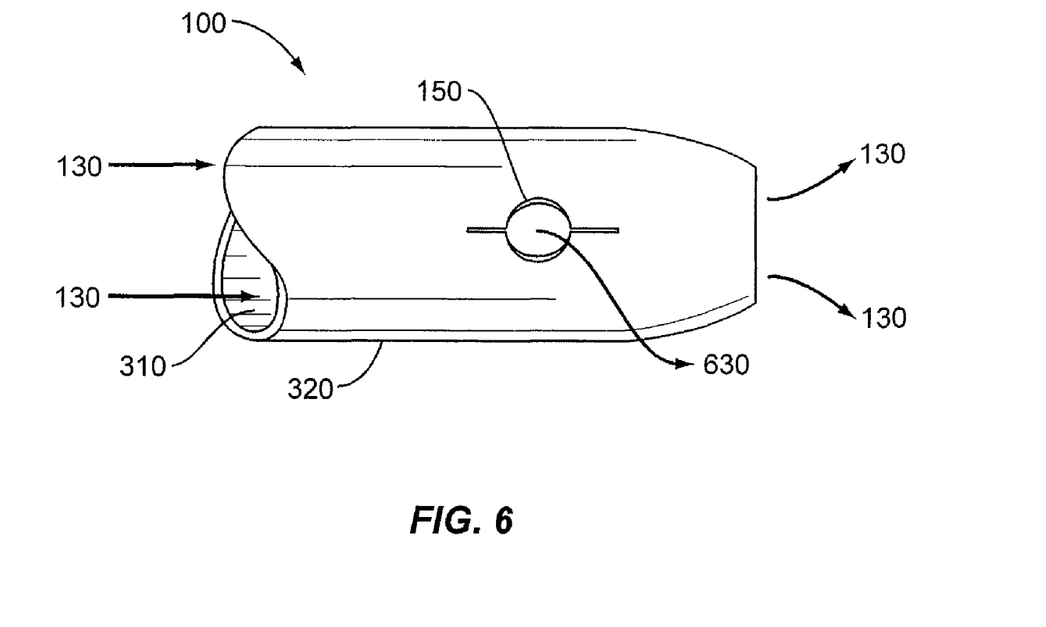
FIG. 6 is a close-up view of another exemplary phacoemulsification irrigation sleeve.

As noted above, the number, positions, and detailed design of the slitted irrigation ports 150 may vary from one embodiment to another. The embodiment pictured in FIGS. 3 and 4 includes one slitted irrigation portion 150 in the shape of a linear slit, oriented along the longitudinal axis of the irrigation sleeve 100, as well as a slitted irrigation port 150 in the shape of a chevron. FIG. 5 illustrates the use of linear slits oriented at an angle relative to the longitudinal axis of the irrigation sleeve 100. The embodiment pictured in FIG. 5 includes two slitted irrigation ports 150 oriented at approximately thirty degrees relative to the axis of the sleeve; other embodiments might include slits oriented at other angles, such as at approximately forty-five degrees. Still other embodiments might include a curved slitted irrigation port 150, e.g., forming a semicircle or other arc.

Figure 7:
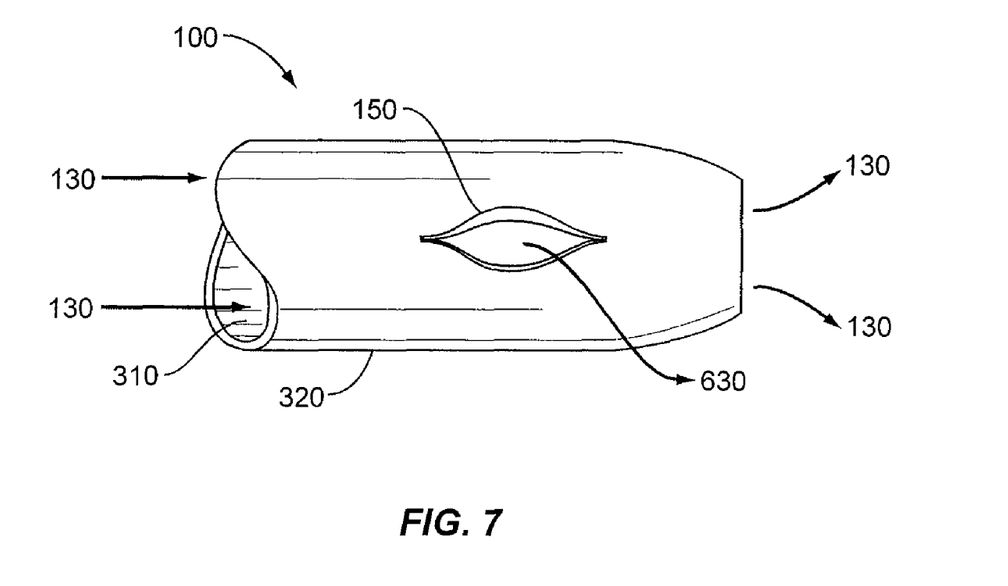
FIG. 7 illustrates the phacoemulsification irrigation sleeve of FIG. 6 with the slitted irrigation port in a splayed configuration.

In some embodiments, a slitted irrigation port 150 may include a slitted portion and an open portion, so that the slitted irrigation port 150 provides a baseline level of flow during normal operation, splaying open to provide additional flow in response to a drop in pressure between the inner and outer surfaces of the irrigation sleeve. An example of this approach is pictured in FIG. 6, which illustrates a slitted irrigation port 150 that includes two slitted portions on either side of an open "hole." As with the other pictured embodiments, irrigation flow follows the path indicated by arrows 130. In this embodiment, however, the baseline flow of irrigation flow also includes flow through the open portion of slitted irrigation port 150, as indicated by arrow 630. As seen in FIG. 7, the slitted irrigation port 150 splays in response to a drop in pressure, thus enlarging the opening and allowing a greater flow of irrigation fluid in the direction indicated by arrow 630.

Figure 8:
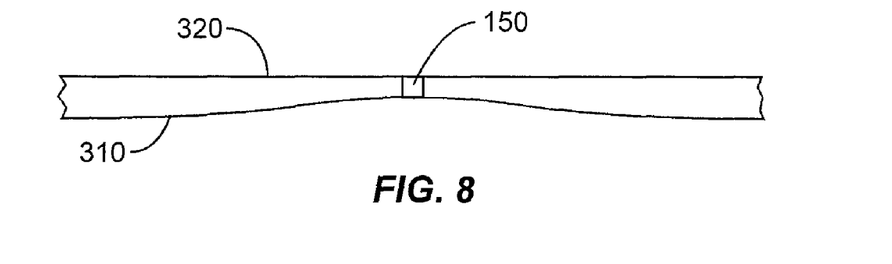
FIG. 8 illustrates a cross-sectional view of the phacoemulsification irrigation sleeve of FIG. 3, taken along line 8-8.

In some embodiments, it may be necessary or helpful to thin the wall of the irrigation sleeve 100 in the vicinity of the slitted irrigation port 150, to enhance the flexibility of the sleeve and achieve the desired degree of splaying. An exemplary approach is shown in FIG. 8, which illustrates a thinned region of the irrigation sleeve 100, adjacent to the slitted irrigation port 150. In the pictured embodiment, the thinning is achieved by tapering the inside surface 310 of the irrigation sleeve 100. However, those skilled in the art will appreciate that other approaches are possible, such as tapering the outside surface 320, or both surfaces.

Figure 9A:
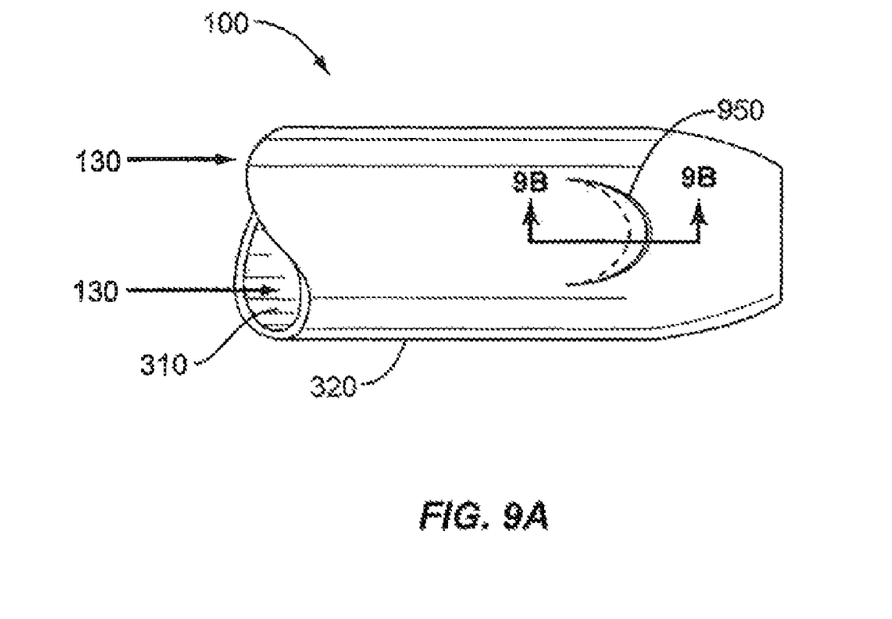
FIGS. 9A and 9B illustrate a side perspective view of another embodiment of a phacoemulsification irrigation sleeve and a cross-sectional view taken along line 9B-9B, respectively.
Figure 9B:
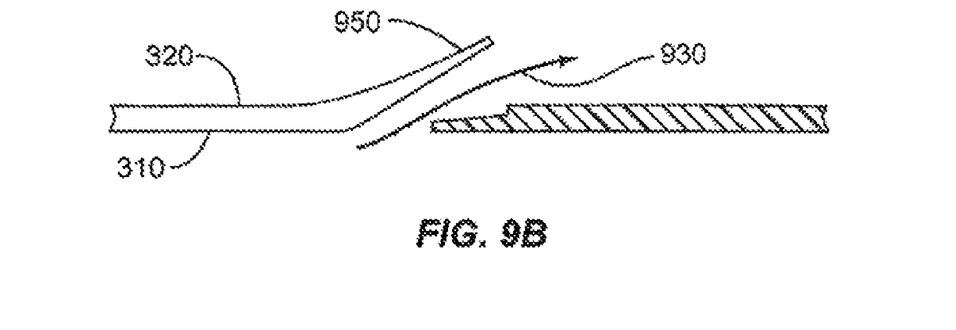

In still other embodiments, a slitted irrigation port 150 may include a flap, or "curtain", that overlaps a portion of the outer surface of the irrigation sleeve, and splays open in response to a drop in pressure between the inner and outer surfaces of the sleeve. One example of this approach is illustrated in FIGS. 9A and 9B. Flap 950 is generally closed during normal operation, allowing little or no flow of irrigation fluid through the port. In response to a drop in pressure, flap 950 opens, allowing additional flow of irrigation fluid in the direction indicated by arrow 930.

The preceding description of various embodiments of a phacoemulsification irrigation sleeve was provided for purposes of illustration and example. Those skilled in the art will appreciate, of course, that the present invention may be carried out in other ways than those specifically set forth herein without departing from essential characteristics of the invention. For instance, two or more of the features described above in connection with different embodiments may be combined on a single embodiment. The present embodiments are thus to be considered in all respects as illustrative and not restrictive, and all changes coming within the meaning and equivalency range of the appended claims are intended to be embraced therein.

What is claimed is:

1. A phacoemulsification system for use in ophthalmic surgery comprising:
   a phacoemulsification needle comprising:
      a hollow shaft;
      a hub formed at a proximal end of the hollow shaft; and
      a lumen extending through the hollow shaft and a flared portion, the lumen defining a opening at a distal end of the hollow shaft; and
   a phacoemulsification irrigation sleeve comprising:
      an elongated, resilient, tubular body section configured to surround the hollow shaft of the phacoemulsification needle, said tubular body section having a distal end and a proximal end, and an inner surface and an outer surface;
      an enlarged section formed on the proximal end of the tubular body section and configured to surround the hub of said phacoemulsification needle and for connection to a phacoemulsification handpiece;
      at least one slitted irrigation port formed adjacent to the distal end of the body section and configured to splay in response to a drop in pressure between the inner surface and the outer surface; and
      an opening formed at the distal end of the tubular body section, the opening remote from the at least one slitted irrigation port, the opening adapted to accommodate a portion of the hollow shaft of the phacoemulsification needle extending through the opening,
      wherein the at least one slitted irrigation port comprises an open portion configured to allow a first flow of irrigation fluid during a phacoemulsification procedure and a slitted portion configured to allow an increased flow of irrigation fluid, relative to the first flow, in response to a drop in pressure between the inner surface and the outer surface of the tubular body section.

2. The phacoemulsification system of claim 1, further comprising a second slitted irrigation port, the second slitted irrigation port comprising:
   a linear slit oriented longitudinally on the tubular body section;
   a linear slit oriented at approximately forty-five degrees relative to the longitudinal axis of the tubular body section;
   an arc-shaped slit; or
   a chevron-shaped slit.

3. The phacoemulsification system of claim 1, further comprising a second slitted irrigation port, the second slitted irrigation port comprising: a flap overlapping a portion of the outside surface of the tubular body section, said flap configured to open in response to a drop in pressure between the inner surface and the outer surface.

4. The phacoemulsification system of claim 1, wherein the tubular body section further comprises a wall, wherein a region of the wall includes a reduced wall thickness adjacent to the at least one slitted irrigation port.

5. A phacoemulsification irrigation sleeve comprising:
   an elongated, resilient, tubular body section configured to surround a portion of a shaft of a phacoemulsification needle, said tubular body section having a distal end and a proximal end, and an inner surface and an outer surface;
   an enlarged section formed on the proximal end of the tubular body section and configured to surround a hub of said phacoemulsification needle and for connection to a phacoemulsification handpiece;
   at least one slitted irrigation port formed adjacent to the distal end of the body section and configured to splay in response to a drop in pressure between the inner surface and the outer surface, the at least one slitted irrigation port comprising:
      an open portion configured to allow a first flow of irrigation fluid during a phacoemulsification procedure; and
      a slitted portion configured to allow an increased flow of irrigation fluid, relative to the first flow, in response to a drop in pressure between the inner surface and the outer surface of the tubular body section.

6. A phacoemulsification system for use in ophthalmic surgery comprising:
   a phacoemulsification needle comprising:
      a hollow shaft;
      a hub formed at a proximal end of the hollow shaft; and
      a lumen extending through the hollow shaft and a flared portion, the lumen defining a opening at a distal end of the hollow shaft; and
   a phacoemulsification irrigation sleeve comprising:
      an elongated, resilient, tubular body portion configured to surround a portion of the hollow shaft of the phacoemulsification needle, said tubular body portion comprising:
         a distal end;
         a proximal end;
         an inner surface; and
         an outer surface;
      an enlarged portion formed on the proximal end of the tubular body portion and configured to surround the hub of said phacoemulsification needle and for connection to a phacoemulsification handpiece;
      at least one slitted irrigation port formed adjacent to the distal end of the tubular body portion and configured to splay in response to a drop in pressure between the inner surface and the outer surface,
      an opening formed at a distal tip at the distal end of the tubular body portion, the opening adapted to accommodate a portion of the shaft of the phacoemulsification needle extending through the opening, wherein the at least one slitted irrigation port comprises an open portion configured to allow a first flow of irrigation fluid during a phacoemulsification procedure and a slitted portion configured to allow an increased flow of irrigation fluid, relative to the first flow, in response to a drop in pressure between the inner surface and the outer surface of the tubular body portion.

7. The phacoemulsification system of claim 6, further comprising a second slitted irrigation port, the second slitted irrigation port comprising:
 a linear slit oriented longitudinally on the tubular body portion;
 a linear slit oriented at approximately forty-five degrees relative to the longitudinal axis of the tubular body portion;
 an arc-shaped slit; or
 a chevron-shaped slit.

8. The phacoemulsification system of claim 6, further comprising a second slitted irrigation port, the second slitted irrigation port comprising: a flap overlapping a portion of the outside surface of the tubular body portion, said flap configured to open in response to a drop in pressure between the inner surface and the outer surface.

9. The phacoemulsification sytem of claim 6, wherein the tubular body portion further comprises at least one thinned region adjacent to the at least one slitted irrigation port.

10. A phacoemulsification irrigation sleeve comprising:
 an elongated, resilient, tubular body section configured to surround a portion of a shaft of a phacoemulsification needle, said tubular body section having a distal end and a proximal end, and an inner surface and an outer surface;
 an enlarged section formed on the proximal end of the tubular body section and configured to surround a hub of said phacoemulsification needle and for connection to a phacoemulsification handpiece; and
 at least one slitted irrigation port formed adjacent to the distal end of the body section and configured to splay in response to a drop in pressure between the inner surface and the outer surface; and
 an opening formed at the distal end of the tubular body section, the opening remote from the at least one slitted irrigation port, the opening adapted to accommodate a portion of the shaft of the phacoemulsification needle extending through the opening,
 wherein the at least one slitted irrigation port comprises an open portion configured to allow a first flow of irrigation fluid during a phacoemulsification procedure and a slitted portion configured to allow an increased flow of irrigation fluid, relative to the first flow, in response to a drop in pressure between the inner surface and the outer surface of the tubular body section.

* * * * *